Figure 1:
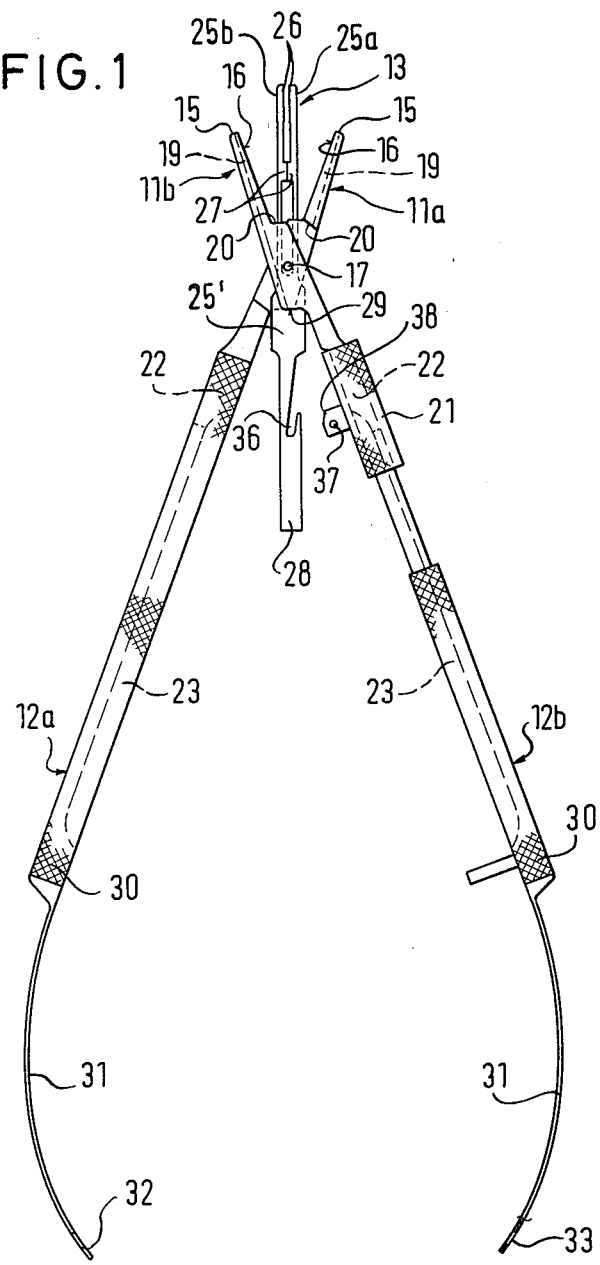

United States Patent [19]

Heiss

[11] Patent Number: 4,478,221

[45] Date of Patent: Oct. 23, 1984

[54] INSTRUMENT FOR USE IN SURGERY

[75] Inventor: Volker Heiss, Tuttlingen, Fed. Rep. of Germany

[73] Assignee: Josef Heiss Medizintechnik GmbH, Fed. Rep. of Germany

[21] Appl. No.: 393,933

[22] Filed: Jun. 30, 1982

[30] Foreign Application Priority Data

Jul. 6, 1981 [DE] Fed. Rep. of Germany ....... 3126578

[51] Int. Cl.³ ............................................. A61B 17/04
[52] U.S. Cl. ................................ 128/334 R; 128/305; 128/340
[58] Field of Search .................. 128/305, 321–322, 128/334, 326, 340

[56] References Cited

U.S. PATENT DOCUMENTS 2,679,249  5/1954  Weihmann ........................... 128/305
2,898,915  8/1959  Kammer ............................... 128/326
4,375,218  3/1983  DiGeronimo ..................... 128/305 X

FOREIGN PATENT DOCUMENTS 393010  6/1933  United Kingdom ................ 128/326

Primary Examiner—Dalton L. Truluck
Attorney, Agent, or Firm—Townsend and Townsend

[57] ABSTRACT

A double limbed suturing instrument for use in surgery has clamping limbs 11a, 11b which can be guided together by the exertion of pressure in order to retain a needle or a thread. Cutting means 13, 14 are provided at one or both of the clamping limbs and can be selectively advanced out of or retracted into the clamping limbs by advancing or retracting a slider 21. The instrument can therefore be used in the normal way to clamp articles and also however to cut threads or the like.

19 Claims, 24 Drawing Figures

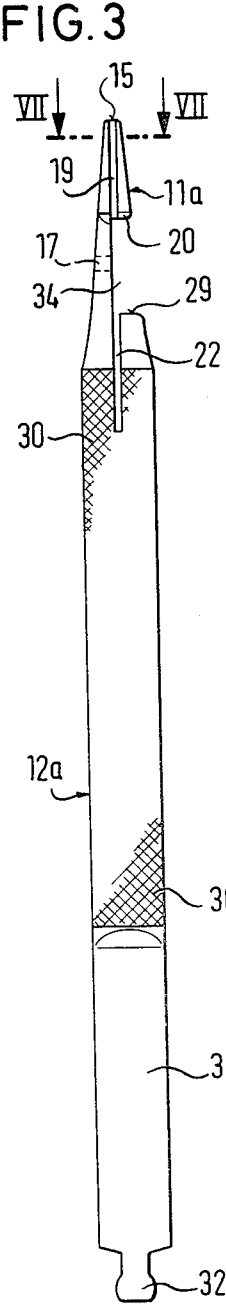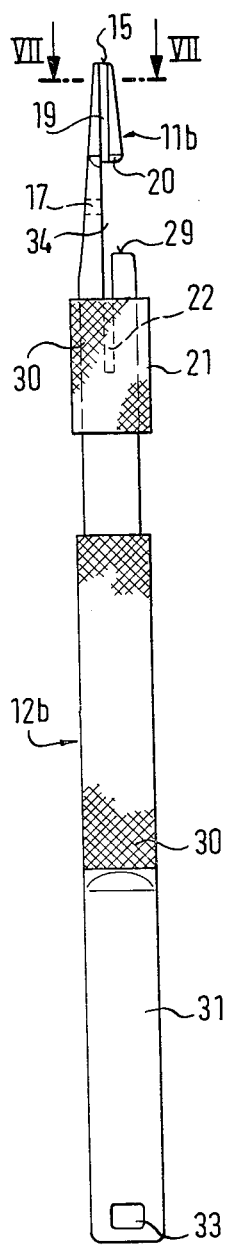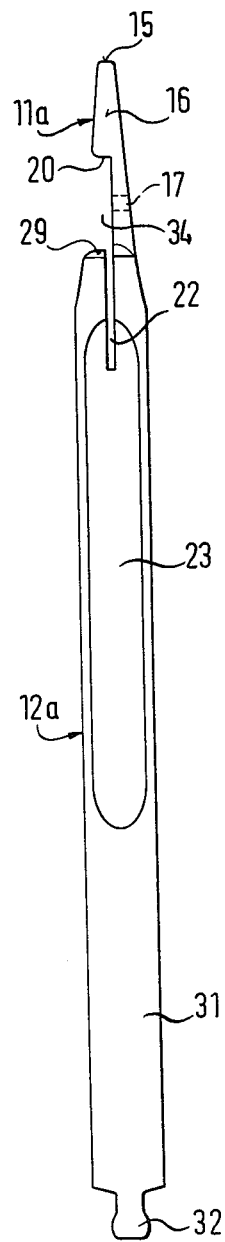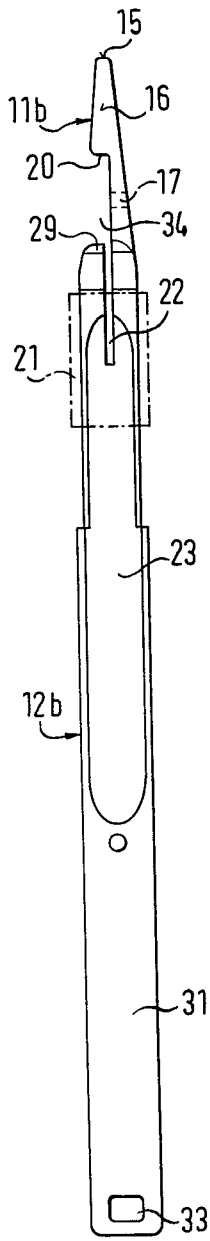

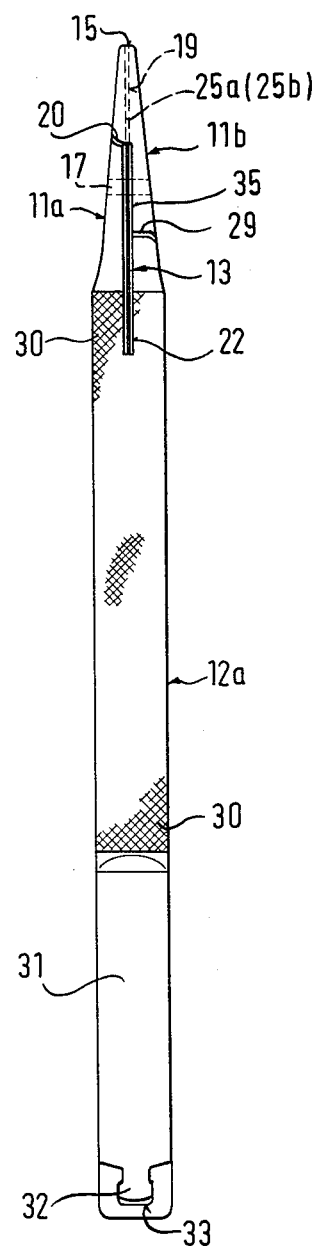

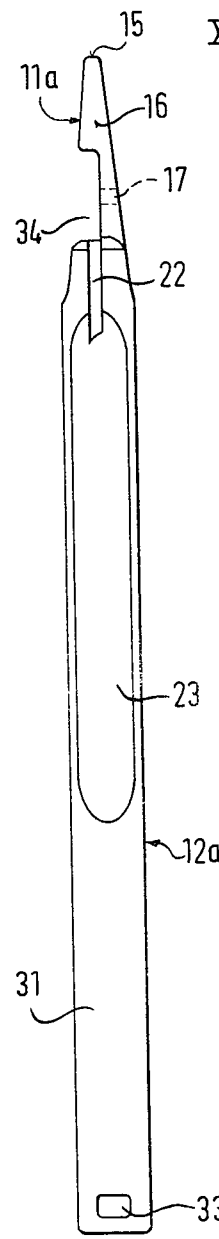
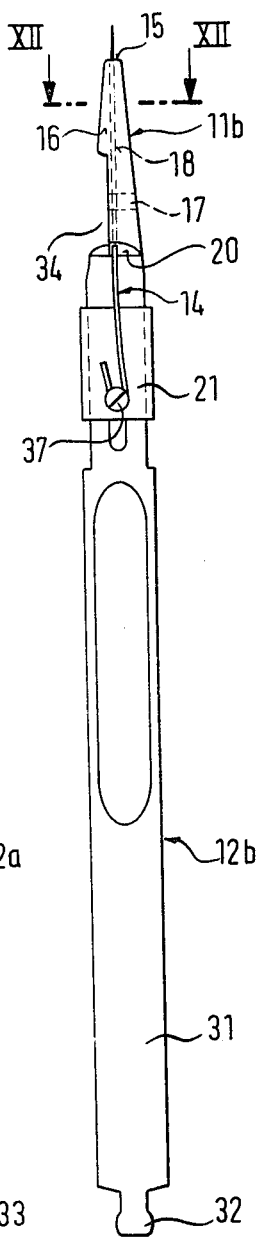
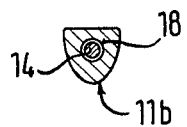
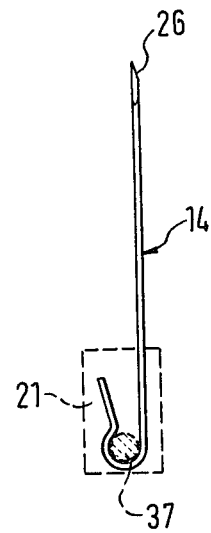

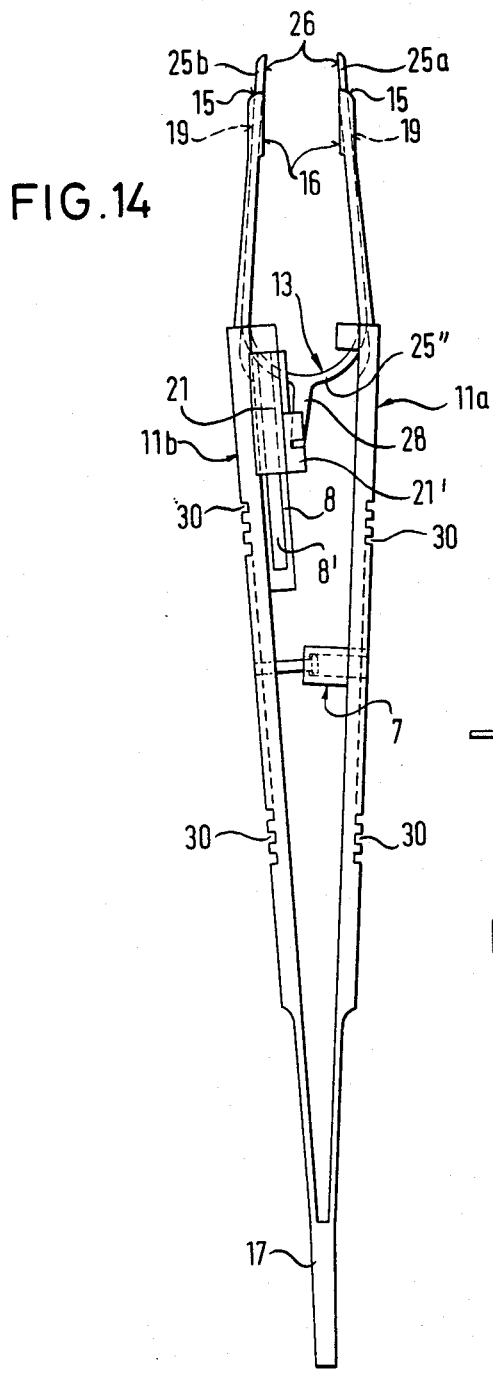
FIG.14
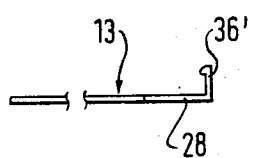
FIG.16
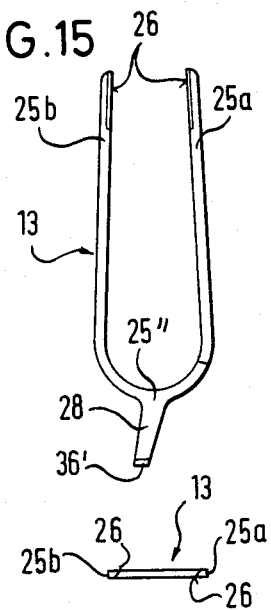
FIG.15
FIG.17

INSTRUMENT FOR USE IN SURGERY

The invention relates to an instrument for use in surgery, in particular microsurgery for performing sutures.

The invention starts from the concept of an instrument comprising a pair of clamping limbs which can be pressed together, preferably against spring bias, to clampingly hold an article such as a thread or a needle between facing clamp surfaces of the clamping limbs, and cutting means provided at at least one of the clamping limbs.

In microsurgery the surgeon requires a needle holder and a pincette in order to produce ligatures. Using a needle holder held in one hand the surgeon guides a suture needle provided with a thread into the tissue while pulling it out again with the pincette which he holds in the other hand. Successive stitches or ligatures are produced by alternately grasping the needle with the needle holder and the pincette. A problem in producing such stitches lies in the fact that after producing the stitch the thread must be cut from the needle. For this purpose the surgeon must generally be passed a further cutting instrument which he can however only grasp and use when he has previously put down the pincette or the needle holder. This procedure is relatively involved and interrupts the rapid progress of the operation.

For this reason one has already constructed a needle holder with a cutting tool (DE-Gbm No. 79 21 108). In order to prevent the cutting tool arranged at the clamping limbs of the needle holder from disturbing the suturing process it must be mounted at a significant distance behind the tips of the clamping limbs of the needle holder. This signifies however that it is necessary to insert the thread a long way into the clamping limbs until it reaches the cutting tool before the thread can be cut. This leads to difficulties particularly when the introduction of the thread between the clamping limbs is made difficult, or indeed impossible, by body organs in the vicinity of the stitch.

The object underlying the present invention is to provide a two-limbed suturing instrument of the initially named kind which makes it possible to avoid changing instruments for the purpose of cutting without the arrangement of the cutting means at the instrument preventing the suturing process and without it being necessary to introduce the thread deep between the clamping limbs in order to cut the same. In other words the combination of the cutting means with the instrument should not in any way hinder the suturing process while cutting should be possible in the same way as when using a normal cutting tool customarily provided for this purpose.

In order to satisfy this object the invention envisages an arrangement in which the cutting means is constructed so that it can be advanced at least up to the tips of the clamping limbs, and preferably considerably beyond these tips, into a working position and so that it can be retracted from the working position to an inoperative position in which it is drawn back behind the tips of the clamping limbs and no longer projects beyond the clamp surfaces.

The invention can be applied both to the pliers-like needle holders and to the pincette which are used for the operation. The thought underlying the invention is to be seen in the fact that the cutting means is movably arranged at the limbs of the instrument in such a way that it can be retracted when using the instrument for suturing into a position in which the suturing process is in no way made more difficult or prevented. In order to cut the thread the cutting means can however be advanced from the rest position to a position near the tips of the clamping jaws. The instrument does not therefore need to be moved in its longitudinal direction in order to cut the thread but can instead be retained in practically the same position as is required to grasp the needle or the thread.

The clamping limbs are preferably formed as portions of respective main limbs of the instrument and the cutting means is preferably advanceably and retractably accommodated in recesses in the main limbs. The cutting means is thus extensively protected so that there is no danger of injury even for the operator.

It is particularly advantageous if the cutting means is not only displaceably but also interchangeably arranged at the limbs of the instrument because cutting means particularly suited to the particular operation can then be inserted into the instrument. The ability to interchange the cutting means is particularly advantageous for ideal cleaning and if the cutting edges become worn.

In a particularly simple embodiment a passage is provided as the recess in one clamping limb with the passage extending in the longitudinal direction of the limb up to the tip of the associated clamping limb and a knife wire is displaceably arranged in the passage as the cutting means. For this purpose a circular bore in one of the limbs is sufficient. The wire preferably has a circular cross-section and is provided with a cutting edge at its end facing the tip.

When the instrument is constructed as a needle holder with the main limbs being connected together at a pivot axle and divided into clamping and manipulating limbs in similar fashion to a pair of pliers a step is provided at the transition from the clamping limb with the passage into the associated manipulating limb with the step extending beyond the passage so that the passage opens inwardly at the step. In this way the knife wire can be moved in its longitudinal direction by a slider. The slider is expediently mounted on the clamping limb and the knife wire is preferably releasably secured to the slider.

It is particularly advantageous if a longitudinal groove is provided in the manipulating limb associated with the clamping limb which is not provided with the passage and if, in the pressed together condition of the two manipulating limbs, the longitudinal groove accommodates the knife wire which emerges from the passage of the other limb. In this way the projecting part of the knife wire does not hinder the movement of the limbs during sewing of the stitch.

It is also advantageous for the longitudinal groove to be followed in the direction remote from the pivot axle by a broader and deeper recess which can accommodate retaining means arranged at the inner side of the slider.

In a specially preferred embodiment, in order to be able to use the instrument of the invention as a pair of scissors, respective grooves are provided as the recesses in the two clamping limbs on the side of the clamp surfaces, with the grooves extending up to the tips, and the cutting means takes the form of a scissor blade having cutting limbs which are displaceably accommodated in the grooves.

The scissor blade usefully has substantially the shape of a tuning fork. An extension of the scissor blade remote from the cutting ends should be releasably secured to a slider which is arranged at one of the clamping or manipulating limbs for movement in the longitudinal direction.

A scissor blade for the instrument of the invention which is economical to manufacture, nevertheless functions well and is simple to clean is characterised in that it consists of a single piece of spring steel. A flat sheet of spring steel is preferably used.

If the instrument of the invention is a needle holder with the main limbs being connected together at a pivot axle and divided into clamping and manipulating limbs in similar manner to a pair of pliers the clamping limbs should have steps at a distance in front of the pivot axle, with the grooves opening into these steps, and the two limbs should lie adjacent one another in the region of the pivot axle with the scissor blade disposed therebetween. In this embodiment a web is provided between the two cutting limbs and should serve as an abutment for the advanced scissor blade at the pivot axle. Furthermore, it is useful if, between the blades and the web, at least one and preferably both the cutting limbs have internal projections which preferably just touch in the rest condition, with the projections serving as an abutment for the retracted scissor blade at the pivot axle. In this manner the movement of the knife blade in both directions is limited by the abutments. In a further advantageous embodiment internal grooves or slots for accommodating the scissor blade are provided in the manipulating limbs so as not to hinder the movement of the manipulating limbs of the needle holder during sewing.

Furthermore, recesses into which the means for securing the scissor blade to the slider can preferably enter can usefully adjoin the slots at the side remote from the pivot axle.

If the instrument of the invention is a pincette a step should be provided in the clamping limbs behind the clamping surfaces and the knife wire should emerge from one of these steps and extend to a slider provided on the associated clamping limb. In this arrangement the slider is preferably arranged in a longitudinal slot of the clamping limb. This results in problemfree guidance without the slider hindering the actuation of the instrument.

If the cutting tool is constructed as a pincette then, in accordance with an advantageous further development of the invention a longitudinal slot guide is arranged at the inside of one of the clamping limbs and the slider connected with the extension is arranged for displacement in the longitudinal direction in the slot guide. In this embodiment the cutting limbs should be connected together at their rear ends by a resiliently flexible web.

Figure 2:
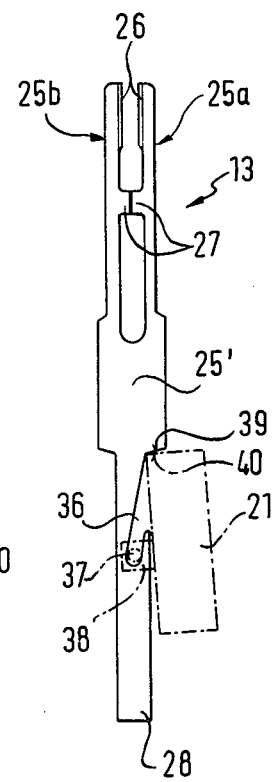
Figure 9:
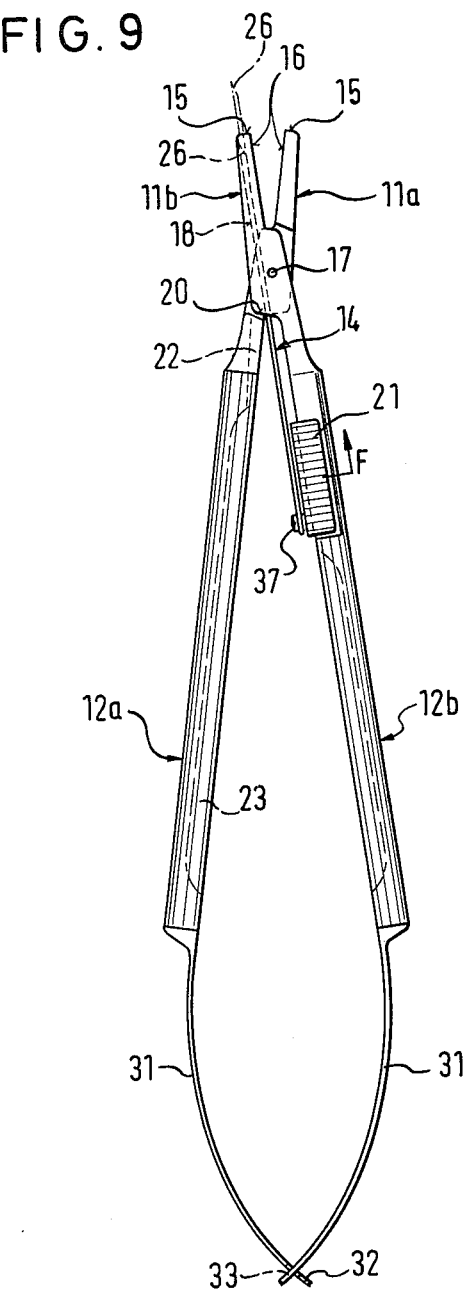
Figure 18:
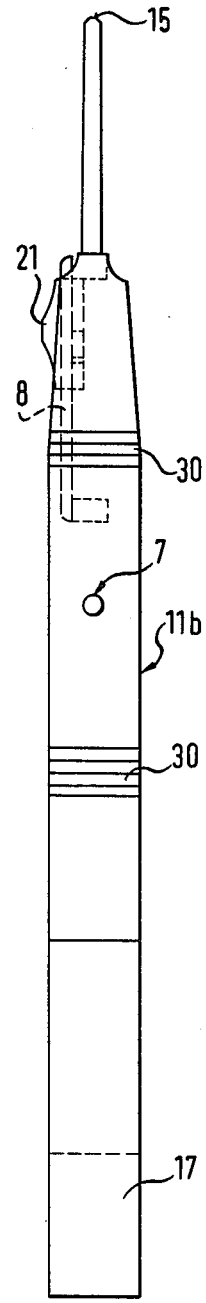
Figure 19:
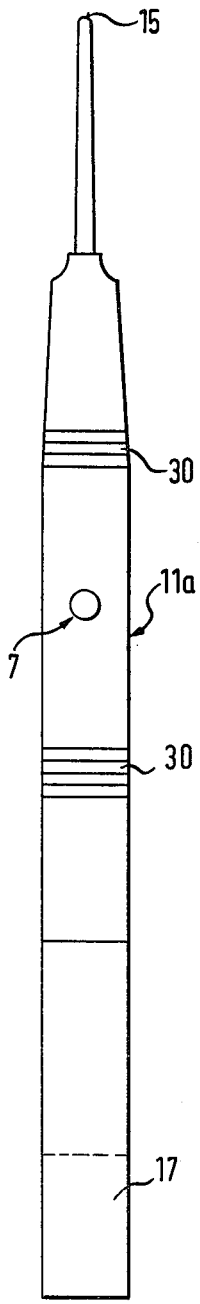
Figure 20:
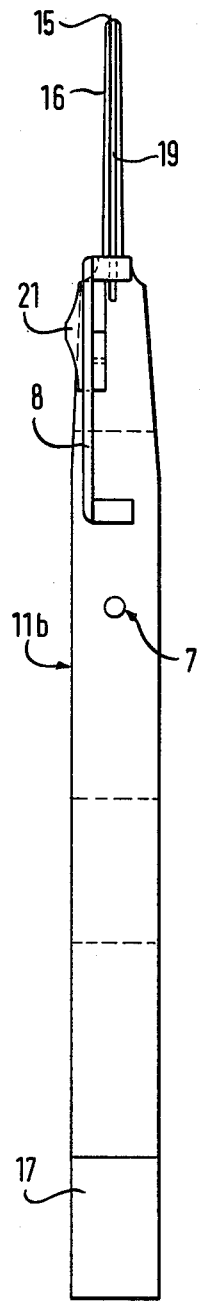
Figure 21:
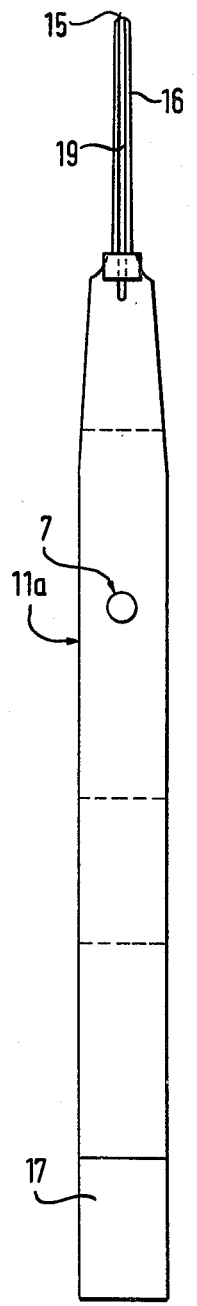
Figure 22:
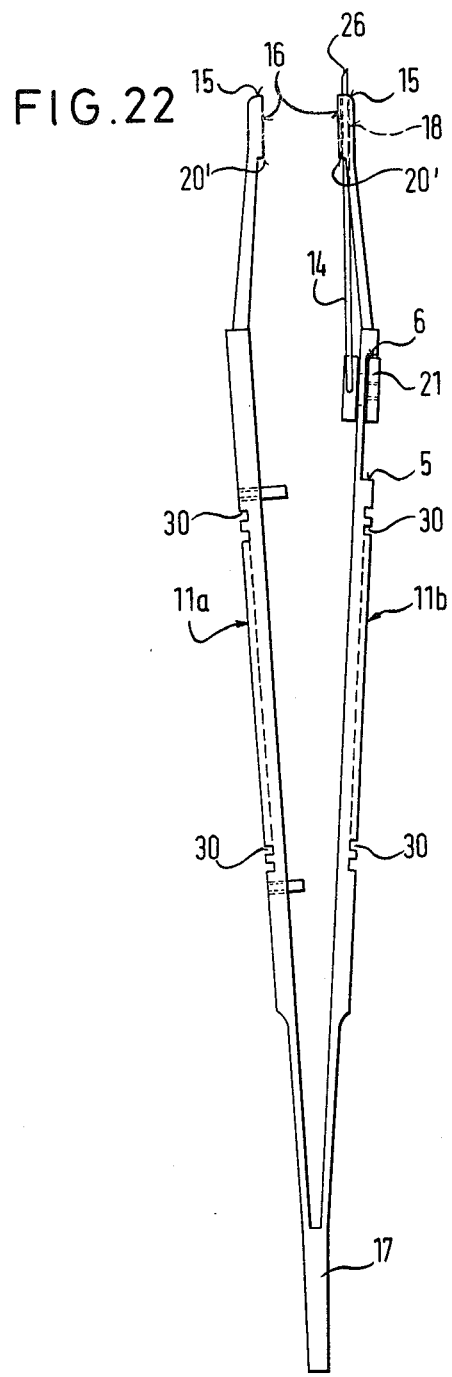
Figure 23:
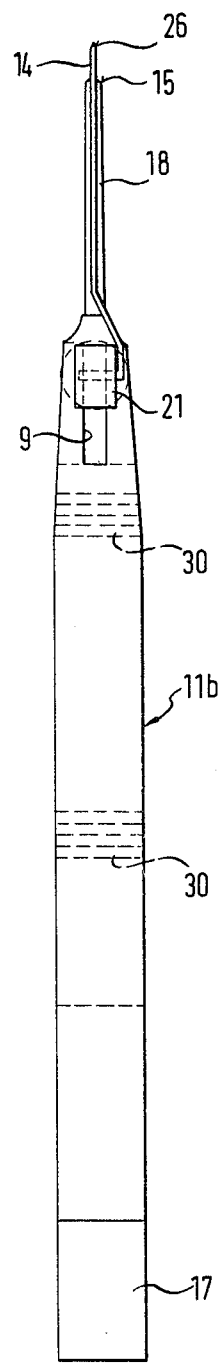
Figure 24:
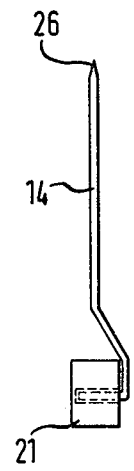

The invention will now be described by way of example in the following with reference to the drawings which show:

FIG. 1 a side view of a first embodiment of a needle holder with a cutting blade in accordance with the invention looking in the direction of the pivot axis 17, FIG. 2 an enlarged view analogous to that of FIG. 1 of the cutting blade that is used and showing the actuating slider 21 in chain-dotted lines, FIGS. 3 to 6 side views of the two limbs of the needle holder shown in FIG. 1 as seen at right angles to the pivot axis from the outside in FIGS. 3 and 4 and from the inside in FIGS. 5 and 6, FIG. 7 a section on the line VII—VII of FIG. 3 or FIG. 4 also showing the associated cutting limb 25a (b), FIG. 8 a side view of the whole needle holder in the closed condition with the view being taken in the same direction as the views of FIGS. 3 and 5, FIG. 9 a view of a further embodiment of a needle holder in accordance with the invention taken in the direction of the pivot axis 17 and showing the use of a knife wire as the cutting means, FIG. 10 an inner view at right angles to the pivot axis 17 of one limb of the needle holder of FIG. 9, FIG. 11 an inner view of the other limb of the needle holder of FIG. 9, FIG. 12 a section on the line XII—XII in FIG. 11 also showing the knife wire 14 inserted in the passage 18, FIG. 13 a detail view of the knife wire used in the embodiment of FIGS. 9 to 12 and showing also the actuating slider 21 in broken lines, FIG. 14 a side view of a first embodiment of a pincette in accordance with the invention having a scissors blade with the view taken in the direction towards the clamping plane, FIG. 15 an enlarged side view analogous to that of FIG. 14 of the scissors blade that is used, FIG. 16 a side view of the scissors blade illustrated in FIG. 15, FIG. 17 an end view of the scissors blade shown in FIGS. 15 and 16 as seen from the cutting side, FIGS. 18 to 21 side views rotated through 90° about the instrument axis relative to FIG. 14 of the two limbs of the pincette shown in FIG. 14 as seen from the outside in FIGS. 18 and 19 and from the inside in FIGS. 20 and 21, FIG. 22 a side view of a further embodiment of a pinette in accordance with the invention and using a knife wire as the cutting means, with the view taken in the direction towards the clamping plane, FIG. 23 a side view rotated relative to FIG. 22 through 90° about the longitudinal axis of the instrument in the direction of the clamping limb 11b carrying the slider 21, and FIG. 24 a detailed view of the knife wire used in the embodiment of FIGS. 22 and 23 together with the slider 21 for actuating this knife wire.

As seen in FIGS. 1 to 8 a first embodiment of a needle holder in accordance with the invention has two main limbs each of which is shown on its own in FIGS. 3, 5 and 4, 6 respectively. Each main limb consists of a clamping limb 11a, 11b and a manipulating limb 12a, 12b. The two main limbs are pivotally connected together at a pivot axle 17 in similar fashion to a pair of pliers. The pivot axle 17 separates the clamping limbs 11a, 11b and the manipulating limbs 12a, 12b from one another.

In the region of the tip 15 the clamping limbs 11a, 11b have clamping surfaces 16 between which a surgical suture needle can be held when the clamping limbs are pressed together.

The outsides of the manipulating limbs are provided with knurling 30 which serves to improve the reliability of the operator's grip on the instrument.

In accordance with the invention shallow grooves 19 with parallel walls which extend in the longitudinal direction of the clamping limbs 11a, 11b are provided on the inner clamping surface sides of these limbs. The cutting limbs 25a, 25b of a scissor blade illustrated in detail in FIG. 2 can be accommodated in these shallow grooves 19. The pliers-like needle holder is shown in FIG. 1 opened beyond the normal open position in order to illustrate the arrangement of the scissor blade 13 between the limbs 11a, 12a and 11b, 12b.

The manipulating limbs 12a, 12b merge at their ends remote from the pivot axle 17 into leaf springs 31 which have a projecting lug 32 and a rectangular opening 33 respectively at their ends remote from the pivot axle 17 so that they can be connected together at this point by insertion of the lug 32 in the opening 33. In the relaxed position of the two leaf springs 31 and after their connection the needle holder of the invention is in its rest position. In this rest position the cutting limbs 25a, 25b contact the bases of the grooves 19 in the manner shown in FIG. 7. The shaping of the limbs 11a, 12a and 11b, 12b as shown in FIGS. 3 to 6 and 8 is of particular importance for the invention. In the region of the pivot axle 17 the material is recessed on one side in the views of FIGS. 3 to 6 so that two steps 20, 29 are formed. Each groove 19 opens outwardly at the step 20. On the other side each groove 19 extends up to the tip 15. The edge of the recess 34 that is formed in this way merges into one flank of the groove 19. On the side remote from the tip 15 the recess returns via the stop 29 to the normal dimensions of the instrument. Each groove 19 is continued as a slot 22 in the associated one of the manipulating limbs 12a, 12b.

In the view of FIG. 8 the two main limbs 11a, 12a and 11b, 12b abut along a substantially Z-like abutment line 35 when the needle holder is in the pressed together condition. As seen in FIG. 8 the two main limbs 11a, 12a and 11b, 12b contact one another with the scissor blade 13 being arranged therebetween. A customary screw or rivet connection can be provided in the area of the pivot axle 17.

As seen in FIGS. 1 and 2 the scissor blade 13 has essentially the external shape of a tuning fork it is however formed in flat spring steel. Respective cutting blades 26 are located at the inside of the cutting ends of the cutting limbs 25a, 25b and the cutting step can be carried out by spring compression of the two cutting limbs 25a, 25b.

Lug-like projections 27 are provided inside the cutting limbs 25a, 25b between the web 25' connecting the two cutting limbs 25a, 25b and the blades 26. In the rest condition of the scissor blade 13 these projections directly contact one another. On resiliently pressing the two cutting limbs 25a, 25b together the projections 27 can move in an overlapped manner past one another so that they do not prevent the cutting step. If desired, the projections 27 can be chamfered off somewhat to facilitate this overlapping process during cutting.

At the end region remote from the blades 26 the scissor blade has a projection 28 which is provided with an angled cut-out 36 at one side. This cut-out serves to receive an actuating pin 37 provided on the rear side of a slider 21 which is arranged on the manipulating limb 12b for displacement in the longitudinal direction thereof. As seen in FIG. 2 the scissor blade 13 can latch onto the slider 21 in such a way that the edge 40 of the slider 21 facing towards the pivot axis 17 snaps behind a step 39 of the scissor blade which is formed at the point of transition of the extension 28 into the two cutting limbs 25a, 25b. The retaining pin 37 is then located in the cut-out 36. In this way a form-locked connection is obtained in the direction of displacement between the slider 21 and the scissor blade 13. In FIG. 1 this connection or coupling between the slider 21 and the scissor blade 13 is shown released. From the position of FIG. 1 the scissor blade 13 can be extracted downwardly which means that the cutting blades 25a, 25b have to be spread somewhat so that the projections 27 can pass the pivot axle 17.

The projections 27 and the web 25' of the scissor blade 13 form the two abutments for limiting the range of displacement of the cutting blade 13 in the two directions.

As, in accordance with FIGS. 1 and 2, the retaining pin 37 is provided on a positioning 38, recesses 23 are provided in the manipulating limbs and in manipulating limb 12a in particular. The recesses 23 follow the slots 22 in the direction remote from the pivot axle 17. In the pressed together condition of the two manipulating limbs 12a, 12b the bearing lug together with the extension 28 can enter into the recess 23. The assembly of the needle holder of the invention and its manner of operation are as follows:

First of all the two main limbs 11a, 12a and 11b, 12b are screwed together along the pivot axle 17 so that a gap remains between them corresponding to the thickness of the scissor blade 13. The scissor blade 13 is then introduced between the two limbs with the two limbs spread apart approximately as shown in FIG. 1. During this step the cutting limbs 25a, 25b are located on respective sides of the pivot axle 17. As soon as the two inner projections 27 abut against the screw forming the pivot axle the cutting limbs 25a, 25b are spread somewhat by hand so that the projections 27 can pass by the pivot axle 17. The scissor blade is now in its working position.

By introducing the retaining pin 37 into the cut-out 36 the snap connection is effected between the slider 21 and the extension 28. In so doing the edge 40 snaps behind the step 39 of the cutting blade 13.

The introduction of the pin 37 in the cut-out 36, is first possible when the two limbs of the needle holder have adopted their rest position. In this condition the lug 32 of the one spring blade is also introduced into the opening 33 of the other spring blade in order to resiliently connect the two limbs together.

The slider 21 can now be displaced between a forward position in which the web 25' contacts the pivot axle 17 and a rearward position in which the projections 27 contact the pivot axle 17. In the first position the blades 26 project significantly beyond the tips 15 of the clamping jaws 11a, 11b of the needle holder so that an effective cutting tool is now available. On pressing together the manipulating limbs 12a, 12b the cutting limbs 25a, 25b are resiliently pressed together so that a thread present between the blades 26 can be cut through as if using a normal cutting tool.

After the thread has been cut through or prior to suturing the slider 21 is retracted which results in the cutting limbs 25a, 25b being retracted in the grooves 19 or in the slots 22 until, at a safe distance from the clamping surfaces of the clamping limbs 11a, 11b they have sunk into the grooves 19 and are accommodated out of harms way. This retracted position of the cutting limbs 25a, 25b is indicated in FIG. 8. As seen from the pivot axle 17 the cutting limbs 25a, 25b extend in the retracted condition only up to approximately ⅔ of the overall length of the clamping limbs 11a, 11b.

It is particularly important for the invention that the grooves 19 become progressively deeper in the direction towards the pivot axle 17 away from the tip 15 so that the cutting limbs 25a, 25b do not project beyond the clamping surfaces of the clamping limbs 11a, 11b in the retracted condition of the scissor blade 13. In this way they do not disturb the needle holding step in any way and there is also no danger of an undesired unintentional cutting action. In the outward direction towards the tip 15 the grooves 19 become shallower so that the blades 26 always emerge from the clamping surfaces 16 when the scissor blade 13 is advanced. Cutting does not therefore only take place in the regions of the cutting limbs 25a, 25b which project beyond the tip 15 but also in the area of the clamping surfaces 16 where the blades 26 already project from the grooves 19 and are therefore effective.

If the blade needs to be exchanged because of wear or for cleaning the extension 28 only needs to be withdrawn from the retaining pin 37 in order to release the snap connection between the slider 21 and the extension 28. By spreading the cutting limbs 25a, 25b the scissor blade 13 can now be withdrawn completely from the main limbs of the needle holder in the reverse manner to that in which it is inserted. A new or cleaned scissor blade can now be inserted. The special advantage of this embodiment thus lies in the fact that, for example for special surgical purposes, special scissor blades can be used with the same needle holder by interchanging them.

In the embodiment of FIGS. 9 to 13 the same reference numerals are used to designate parts which have counterparts in the preceding embodiment.

In the present case it is however not a scissor blade but instead a knife wire 14 which is provided as the cutting tool. This knife wire 14 is shown in detail in FIG. 13. At its end remote from the pivot axis 17 it is bent into a semicircle so that it can be fastened to a retaining pin 37 provided at the slider 21. The retention of the knife blade on the slider 21 preferably takes place using a kind of latch connection in which the bent end of the knife blade resiliently snaps onto the pin 37 as indicated in FIG. 13.

The larger part of the knife wire 14 is straight and has a circular cross-section. The knife wire 14 is provided with a cutting edge 26 at the end remote from the point of attachment 37.

In order to displaceably house the knife wire 14 in the longitudinal direction of the clamping limb 11b a passage 18 is provided in the clamping limb 11b and extends in the longitudinal direction thereof. This passage opens in the present embodiment at a step 20 which, as seen from the tip 15 finishes on the far side of the pivot axle 17. From there on the knife wire 14 is inserted in the passage 18. The slider 21 is displaceable on the manipulating limb 12b parallel to the passage 18. The knife wire 14 is moved in the axial direction by displacement of the slider 21.

As seen in FIG. 9 a longitudinal groove 22 and a subsequent recess 23 are provided in the manipulating limb 12a. When the instrument is pressed together the knife wire 14 and the securing pin 37 engage into the longitudinal groove 22 and the recess 23 respectively.

When using the needle holder of FIGS. 9 to 13 the slider 21 is first of all arranged in the retracted position shown in FIG. 9 in which the blade 26 is reliably sunk inside the passage 18. The instrument can now be used as a classical needle holder. If now, at the end of the suturing step the thread is to be cut the operator pushes the slider 21 forwardly in the direction of the arrow F whereby the blade 26 emerges from the passage 18 in the manner shown in broken lines in FIG. 9 and can be used as a cutting tool.

In the following figures the same reference numerals will also be used to designate parts which have counterparts in the previous embodiments.

FIGS. 14 to 21 show the application of the invention to a pincette having two clamping limbs 11a, 11b which are rigidly connected together at 17 at their rear ends and which can be resiliently pressed together by grasping and pressing on the grooved portions 30.

In accordance with the invention shallow grooves 19 in which the cutting limbs 25a and 25b of a scissor blade shaped in accordance with FIG. 15 slidingly engage are once again provided in the front ends of the clamping limbs 11a, 11b.

The two cutting limbs 25a, 25b are connected together by a rounded web 25″ at their ends remote from the blades 26. From here an extension 28 having a hook-like end 36′ branches off rearwardly. The hook-like end 36′ engages in a complementary formation 21′ of a slider 21 which is arranged to slide in the longitudinal direction in an elongate slot guide 8. The elongate slot guide 8 is arranged at the inner side of the clamping limb 11b in the region between the clamp surface 16 and the rear connection 17 between the clamping limbs. The longitudinal slot 8′ in the longitudinal slot guide has a length such that the blades 26 can be advanced forwardly beyond the clamp surfaces 16 while, in the retracted condition of the slider 21 they disappear inside the grooves 19 and are not able to prevent articles being clamped between the clamp surfaces 16.

A guide connection 7 between the clamping limbs 11a, 11b limits the extent to which the clamping limbs 11a, 11b can be spread apart so that movement of the scissor blade 13 out of the grooves 19 is prevented. The rounded web 25″ must be sufficiently flexible that, on pressing together the clamping limbs 11a, 11b, the scissor blade can be compressed until the blades 26 come into contact. The shape of the blades 26 in accordance with the invention can be seen from the end view of FIG. 17.

In the advanced position of the scissor blade 13 illustrated in FIG. 14 the cutting limbs 25a, 25b project forwardly beyond the tips 25 of the clamping limbs 11a, 11b so that on pressing together the clamping limbs 11a, 11b the cutting edges 26 are guided towards one another and are able to separate an article such as thread introduced therebetween.

If the slider 21 is retracted along the longitudinal slot guide 8 the cutting limbs 25a, 25b disappear completely within the grooves 19.

FIGS. 22 to 24 show the use of the invention with a pincette with two clamping limbs 11a, 11b which serve simultaneously for gripping but in which a knife wire illustrated in detail in FIG. 24 is axially displaceably arranged in a longitudinally extending passage 18 at the tip 15 of only one of the clamping limbs 11b. The rear end of the knife wire 14 is bent round and secured in the manner shown in FIG. 24 to a slider 21 which, as shown in FIGS. 22 and 23, is displaceably secured in the longitudinal direction by means of a longitudinal slot 9 in the front region of the clamping limb 11b.

Behind the clamp surfaces 16 the clamping limbs 11a, 11b are recessed outwardly sufficiently far that the circular part of the knife wire 14 emerges rearwardly from the step 20′ that is formed and extends to the slider 21 where it is pivotally attached about an axis at right angles to the plane of FIG. 22.

In the position shown in FIGS. 22 and 23 the slider 21 is advanced as far as possible and contacts an abutment 6 (FIG. 22) of the limb 11b. The knife wire 14 now projects sufficiently far beyond the tip 15 of the associated limb 11b that the cutting edge 26 can be used for cutting.

If the slider 21 is now fully retracted until it contacts the rear abutment 5 of the limb 11b the blade 26 disappears completely inside the longitudinal passage 18 and no longer prevents the use of the pincette to clamp articles between the clamping surfaces 16.

I claim:

1. An instrument for use in surgery, and in particualr microsurgery, for performing suturing, comprising:
   a pair of elongate clamping members secured one to the other for pivotal movement abut a pivot point one in relation to the other between an open position, wherein facing inner surfaces of each member are angularly spaced one from the other, and a clamping position, wherein said facing inner surfaces of each member are brought into substantially parallel abutment one with the other to clampingly hold an article therebetween, at least one of said members including an elongate recess formed along an inner surface axis, said inner surfaces extending along said members on a first side of said pivoed on at least one of said clamping limbs, said cutting means being relatively movable between a retracted position within said elongate recess and an extended position projecting beyond a clamp member tip portion.

2. An instrument in accordance with claim 1 further comprising:
   a passage provided as the recess in one clamping limb, the passage extending in a longitudinal limb direction up to the tip portion of the associated clamping limb; and
   a knife wire displaceably arranged in the passage as the cutting means.

3. An instrument in accordance with claim 2 and constructed as a needle holder wherein the main limbs are connected together at a pivotal axle and divided into clamping and manipulating limbs, further comprising:
   a step provided at a transition point from clamping limb having the passage into the associated manipulating limb, and having the step extending beyond the passage so that the passage opens inwardly at the step.

4. An instrument in accordance with claim 3, further comprising;
   a slider to which the knife wire is releasably fastened at the manipulating limb.

5. An instrument in accordance with claim 4, further comprising:
   a longitudinal groove provided in the manipulating limb associated with the clamping limb which is not provided with the passage; and the longitudinal groove accommodating the knife wire which emerges from the passage of the other limb when the facing inner surfaces are brought into substantially parallel abutment in the clamping position.

6. An instrument in accordance with claim 5, wherein the longitudinal groove is followed in a direction remote from the pivot axle by a broader and deeper recess for accommodating a retaining means at the inner side of the slider.

7. An instrument in accordance with claim 1, further comprising:
   respective grooves provided as recesses in the two clamping limbs on the side of the facing surfaces, the grooves extending up to the tips; and
   wherein the cutting means comprises a scissor blade having cutting limbs which are longitudinally displaceably accommodated within the grooves.

8. An instrument in accordance with claim 7 wherein the scissor blade has substantially the shape of a tuning fork.

9. An instrument in accordance with claim 7 wherein the scissor blade has an extension bracket remote from the cutting limbs, and
   a slider releasably secured to said scissor blade for displacement of said scissor blade in a longitudinal direction along one of said clamping members.

10. An instrument in accordance with claim 7, wherein the scissor blade consists of a single piece of spring steel.

11. An instrument in accordance with claim 7 and constructed as a needle holder with the main limbs being connected together at a pivot axle and divided into clamping and manipulating limbs, wherein the clamping limbs have steps at a distance in front of the pivot axle; wherein grooves open into said steps; and wherein the clamping members lie adjacent one another in the region of the pivot axle with the scissor blade disposed therebetween.

12. An instrument in accordance with claim 11, further comprising:
   a web positioned between the two cutting limbs as an abutment for the scissor blade.

13. An instrument in accordance with claim 13, wherein at least one of the cutting limbs has internal projections which just touch in the retracted position, the projections serving as an abutment for the retracted scissor blade at the pivot axle.

14. An instrument in accordance with claim 11, further comprising:
   internal grooves for accommodating the scissor blade located in the manipulating limbs.

15. An instrument in accordance with claim 14, further comprising:
   steeper and broader recesses adjoining the grooves at the side remote from the pivot axle.

16. An instrument in accordance with claim 2 which is constructed as a pincette, further comprising:
   a step provided in the clamping limbs behind the clamping surfaces; and
   wherein the knife wire emerges from said step and extends to a slider provided on the associated clamping limb.

17. An instrument in accordance with claim 16, wherein the slider is arranged in a longitudinal slot of the clamping limb.

18. An instrument in accordance with claim 9 which is constructed as a pincette, further comprising:
   a longitudinal slot guide arranged at the inside of one of the clamping limbs; and
   wherein the slider is connected with the extension and arranged for displacement in a longitudinal direction in the slot guide.

19. An instrument in accordance with claim 18, wherein the cutting limbs are connected together at their rear ends by a resiliently flexible web.

* * * * *